United States Patent
Kim et al.

(10) Patent No.: US 9,863,835 B2
(45) Date of Patent: Jan. 9, 2018

(54) HOLE DETECTION METHOD OF VEHICLE AND SYSTEM PERFORMING THE SAME

(71) Applicants: Hyundai Motor Company, Seoul (KR); IUCF-HYU (Industry-University Cooperation Foundation Hanyang University), Seoul (KR)

(72) Inventors: Tae Ho Kim, Seoul (KR); Yunsang Kwak, Gyeonggi-do (KR); Sangkeun Ahn, Seoul (KR); Junhong Park, Gyeonggi-do (KR)

(73) Assignees: Hyundai Motor Company, Seoul (KR); IUCF-HYU (Industry-University Cooperation Foundation Hanyang University), Seoul (KR)

( * ) Notice: Subject to any disclaimer, the term of this patent is extended or adjusted under 35 U.S.C. 154(b) by 0 days.

(21) Appl. No.: 15/146,991

(22) Filed: May 5, 2016

(65) Prior Publication Data
US 2017/0089801 A1    Mar. 30, 2017

(30) Foreign Application Priority Data
Sep. 24, 2015    (KR) .................. 10-2015-0135845

(51) Int. Cl.
| | |
|---|---|
| *G01M 3/24* | (2006.01) |
| *G01M 17/00* | (2006.01) |
| *G01N 29/12* | (2006.01) |

(52) U.S. Cl.
CPC .............. *G01M 3/24* (2013.01); *G01M 17/00* (2013.01); *G01N 29/12* (2013.01)

(58) Field of Classification Search
CPC ........ G01M 3/24; G01M 17/00; G01N 29/44; G01N 29/12
See application file for complete search history.

(56) References Cited

U.S. PATENT DOCUMENTS

| | | | | |
|---|---|---|---|---|
| 4,719,801 A | * | 1/1988 | Blaser | G01L 3/24 73/40 |
| 4,901,576 A | * | 2/1990 | Rademacher | G01M 3/24 73/588 |
| 5,925,816 A | * | 7/1999 | Kovacs | G01M 3/146 73/40 |
| 6,983,642 B2 | * | 1/2006 | Stumpf | G01M 17/007 73/40.5 A |
| 7,987,720 B2 | * | 8/2011 | Gayle | G01N 29/348 73/40.5 A |

(Continued)

FOREIGN PATENT DOCUMENTS

| | | |
|---|---|---|
| JP | H04184133 A | 7/1992 |
| JP | 2003-065880 A | 3/2003 |

*Primary Examiner* — Michael J Zanelli
(74) *Attorney, Agent, or Firm* — Mintz Levin Cohn Ferris Glovsky and Popeo, P.C.; Peter F. Corless

(57) ABSTRACT

A hole detection method of a vehicle and a system performing the same may include positioning an air injection nozzle at a predetermined position of a vehicle body and positioning a sound sensor at a position corresponding to the air injection nozzle, injecting an air jet from the air injection nozzle, detecting a sound wave from the sound sensor, and calculating a characteristic of a water leakage hole formed on the vehicle body by using the sound wave detected from the sound sensor.

9 Claims, 8 Drawing Sheets

(56) References Cited

U.S. PATENT DOCUMENTS

| | | |
|---|---|---|
| 8,950,261 B2 | 2/2015 | Carradori et al. |
| 2007/0109138 A1* | 5/2007 | Farrell .................... G01M 3/24 340/605 |

* cited by examiner ary embodiment of the present invention may include positioning an air injection nozzle at a predetermined position of a vehicle body and positioning a sound sensor at a position corresponding to the air injection nozzle, injecting an air jet from the air injection nozzle, detecting a sound wave from the sound sensor, and calculating a characteristic of a water leakage hole formed on the vehicle body by using the sound wave detected from the sound sensor.

HOLE DETECTION METHOD OF VEHICLE AND SYSTEM PERFORMING THE SAME

CROSS-REFERENCE TO RELATED APPLICATION

This application claims under 35 U.S.C. §119(a) the benefit of Korean Patent Application No. 10-2015-0135845 filed in the Korean Intellectual Property Office on Sep. 24, 2015, the entire contents of which are incorporated herein by reference.

BACKGROUND (a) Field of the Invention

The present invention relates to a hole detection method of detecting a water leakage hole of a welding portion, a window, and/or a vehicle body of a vehicle, and a system performing the same.

(b) Description of the Related Art

In vehicle manufacturing, water leakage of a vehicle body must be detected, so that the cause of the water leakage can be determined and repaired.

Tiny holes in a panel or a window enable air or water to enter the vehicle and generate a wind sound during driving.

Conventionally, to find such holes, water has been sprinkled on the vehicle body and water leakage has been confirmed manually, but it is not easy to find the holes by this method.

Recently, a method of installing a sound wave generator (audible sound pressure or ultrasonic wave) in the vehicle and detecting water leakage holes by measuring noise leaking from the holes has been used.

However, when output of the sound wave generator is low, reliability may be deteriorated, and other parts except the leakage holes must be closed and sealed to precisely measure the water leakage part.

The above information disclosed in this Background section is only for enhancement of understanding of the background of the invention and therefore it may contain information that does not form the prior art that is already known in this country to a person of ordinary skill in the art.

SUMMARY

The present invention provides a hole detection method of a vehicle and a system performing the same having advantages of precisely detecting water leakage parts regardless of a closed and/or sealed state of the various parts and/or output of a sound wave generator.

A hole detection method of a vehicle and a system performing the same according to an exemplary embodiment of the present invention may include positioning an air injection nozzle at a predetermined position of a vehicle body and positioning a sound sensor at a position corresponding to the air injection nozzle, injecting an air jet from the air injection nozzle, detecting a sound wave from the sound sensor, and calculating a characteristic of a water leakage hole formed on the vehicle body by using the sound wave detected from the sound sensor.

The characteristic of the water leakage hole formed on the vehicle body may be calculated by using output noise or frequency of the sound wave detected from the sound sensor.

The air injection nozzle may be disposed at one surface of the vehicle body at a predetermined distance therefrom.

The sound sensor may be disposed at the opposite side of the air injection nozzle on the basis of the vehicle body at a predetermined distance from the vehicle body.

The air injection nozzle may inject air in a perpendicular direction with respect to a thickness direction of the vehicle body. A water leakage hole characteristic may include an interior diameter.

A hole detection system of a vehicle according to an exemplary embodiment of the present invention may include an air injection nozzle disposed at a predetermined position of a vehicle body to inject an air jet, a sound sensor disposed to detect a sound wave generated by the air jet injected from the air injection nozzle, and a controller calculating existence or nonexistence and characteristics of a water leakage hole formed on the vehicle body according to characteristics of the sound wave detected from the sound sensor.

The system may include a moving portion set up to move the air injection nozzle or the sound sensor to a predetermined position of the vehicle body.

The air injection nozzle and the sound sensor may be disposed at opposite sides on the basis of the vehicle body and disposed at a predetermined distance therefrom.

The characteristics of the water leakage hole formed on the vehicle body are calculated by using output noise or frequency of the sound wave detected from the sound sensor.

The air injection nozzle injects air in a perpendicular direction with respect to a thickness direction of the vehicle body.

The controller may include an amplifier amplifying the sound wave detected from the sound sensor, a data processor processing data of the sound signal amplified by the amplifier, and a calculator calculating existence or nonexistence and the characteristics of the water leakage hole by using data processed at the data processor.

The controller may detect characteristics of the sound wave detected from the sound sensor, and calculate existence or nonexistence and the characteristics of the water leakage hole formed on the vehicle body by comparing the detected sound wave characteristics and previously stored reference sound wave characteristics.

According to the present invention to attain this purpose, water leakage parts may be precisely detected regardless of a closed and sealed state and output of a sound wave generator by injecting an air jet and measuring noise generated from a water leakage hole.

DETAILED DESCRIPTION OF THE EMBODIMENTS

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Throughout the specification, unless explicitly described to the contrary, the word "comprise" and variations such as "comprises" or "comprising" will be understood to imply the inclusion of stated elements but not the exclusion of any other elements. In addition, the terms "unit", "-er", "-or", and "module" described in the specification mean units for processing at least one function and operation, and can be implemented by hardware components or software components and combinations thereof.

Further, the control logic of the present invention may be embodied as non-transitory computer readable media on a computer readable medium containing executable program instructions executed by a processor, controller or the like. Examples of computer readable media include, but are not limited to, ROM, RAM, compact disc (CD)-ROMs, magnetic tapes, floppy disks, flash drives, smart cards and optical data storage devices. The computer readable medium can also be distributed in network coupled computer systems so that the computer readable media is stored and executed in a distributed fashion, e.g., by a telematics server or a Controller Area Network (CAN).

An exemplary embodiment of the present invention will hereinafter be described in detail with reference to the accompanying drawings.

Figure 1:
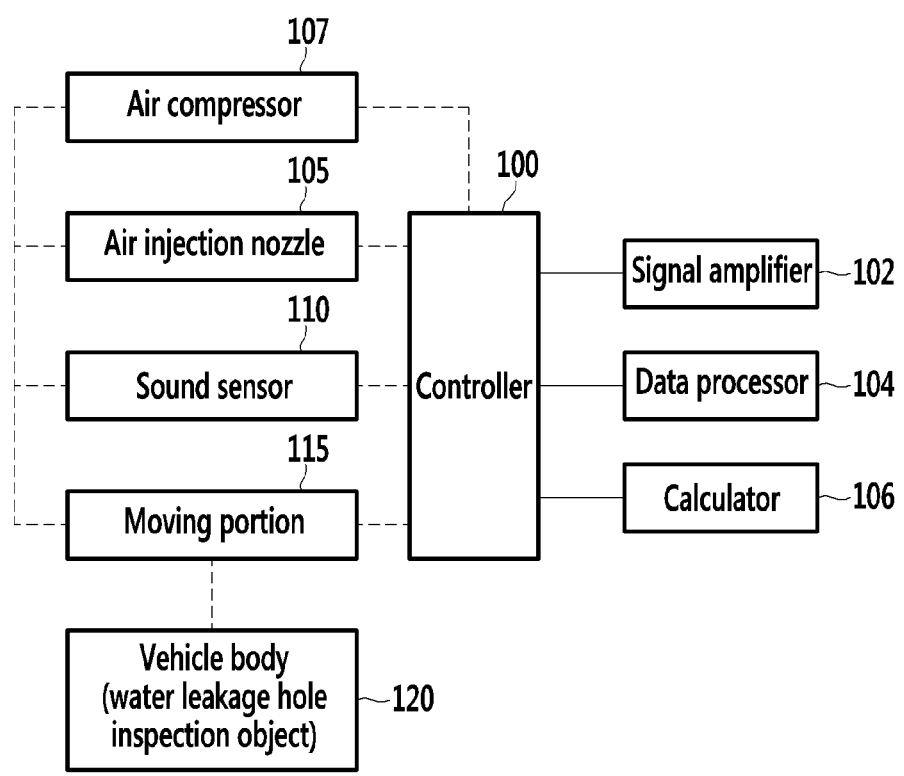
FIG. 1 is a block diagram showing constituent elements of a hole detection system of a vehicle according to an exemplary embodiment of the present invention.

FIG. 1 is a block diagram showing constituent elements of a hole detection system of a vehicle according to an exemplary embodiment of the present invention.

Referring to FIG. 1, a hole detection system of a vehicle includes an air compressor 107, an air injection nozzle 105, a sound sensor 110, a moving portion 115, and a controller 100. An inspection object can be, for example, a vehicle body 120 having a water leakage hole 200, and the controller 100 includes a signal amplifier 102, a data processor 104, and a calculator 106.

The water leakage hole 200 may be formed on the vehicle body 120, and the hole detection system preferably detects a position and size of the water leakage hole 200.

The air compressor 100 compresses and injects air from the air injection nozzle 105, and the air injection nozzle 105 injects an air jet to parts where the water leakage hole 200 is formed.

The sound sensor 110 detects a sound wave caused by the air injection nozzle 105 to be detected from the water leakage hole 200, and the moving portion 115 may move the air injection nozzle 105 and the sound sensor 110 to a predetermined position, respectively.

The controller 100 may control the air compressor 100, the air injection nozzle 105, and the moving portion 115, respectively, and a position and size of the water leakage hole 200 may be detected and calculated by using the sound wave signal generated from the sound sensor 110.

The signal amplifier 102 may amplify the sound wave signal detected from the sound sensor 110, the data processor 104 may process the amplified sound wave signal and extract data, and the calculator 106 may calculate a position and size of the water leakage hole 200 by using the extracted data.

Further, the calculator 106 may calculate a position and size of the water leakage hole 200 by comparing previously stored reference data and the detected actual data.

Figure 2:
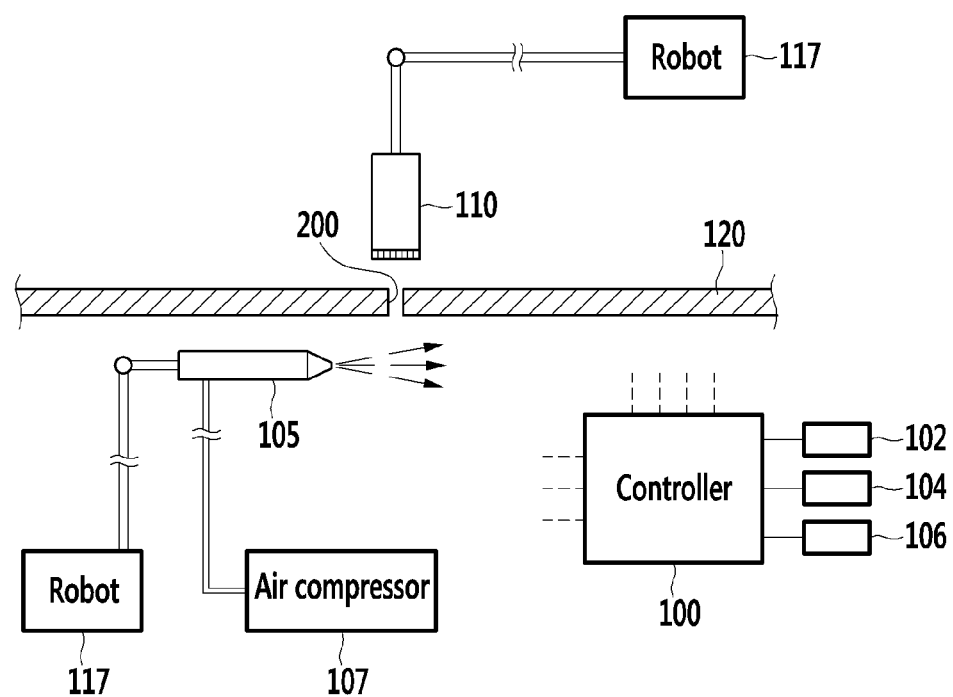
FIG. 2 is a schematic diagram showing a hole detection system of a vehicle according to an exemplary embodiment of the present invention.

FIG. 2 is a schematic diagram showing a hole detection system of a vehicle according to an exemplary embodiment of the present invention.

Referring to FIG. 2, the water leakage hole 200 is formed on the vehicle body 120, and a robot 117 moves the sound sensor 110 and the air injection nozzle 105 to a predetermined position of the vehicle body 120. Further, the air injection nozzle 105 injects air generated from the air compressor 107.

The controller 100 amplifies the sound signal detected from the sound sensor 110, processes the data, and calculates a position and size of the water leakage hole 200.

According to an exemplary embodiment of the present invention, the controller 100 may be realized as at least one microprocessor operating by a predetermined program, and the predetermined program may include a series of commands for performing a following method according to an exemplary embodiment of the present invention.

Figure 3:
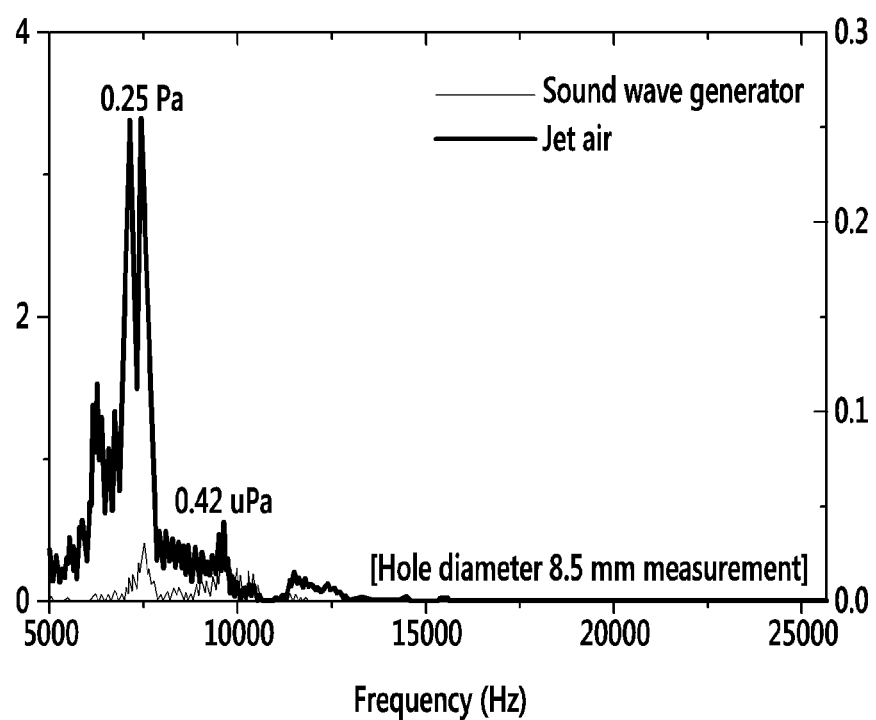
FIG. 3 and FIG. 4 are graphs showing a characteristic and size of a water leakage hole according to an air jet according to an exemplary embodiment of the present invention.
Figure 4:
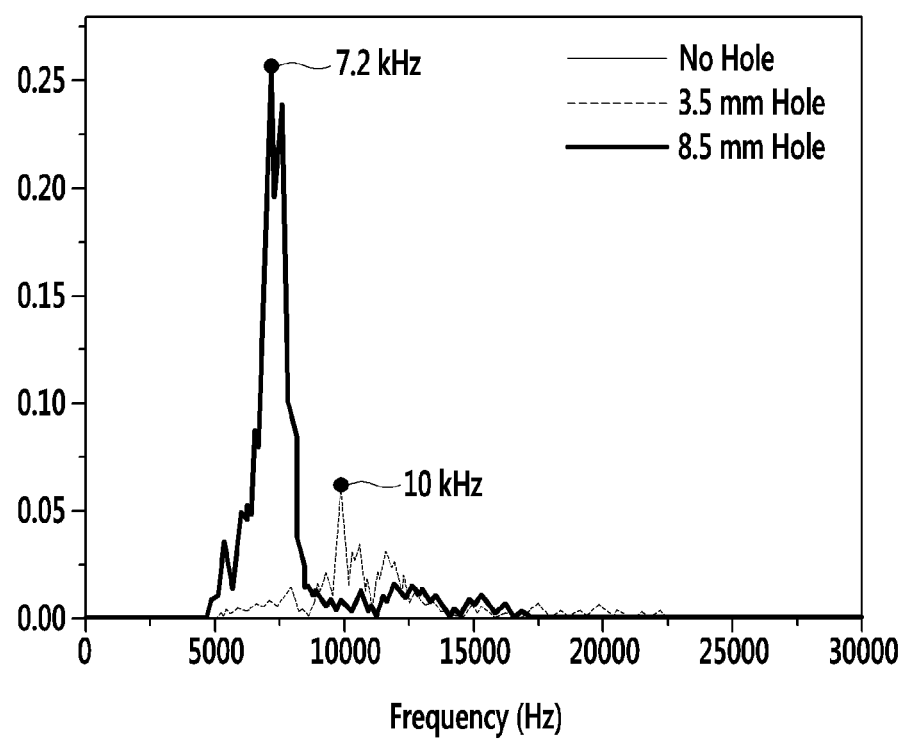

FIG. 3 and FIG. 4 are graphs showing a characteristic and size of a water leakage hole according to an air jet according to an exemplary embodiment of the present invention.

Referring to FIG. 3, the horizontal axis represents a frequency detected from the sound sensor 110, and the vertical axis represents sound pressure.

In particular, sound pressure is low when using a sound wave generator according to the conventional art, and sound pressure is relatively high when an air jet is injected to a water leakage part by using the air injection nozzle 105 according to an exemplary embodiment of the present invention. Here, the diameter of the water leakage hole is about 8.5 mm.

Referring to FIG. 4, the horizontal axis represents a frequency detected from the sound sensor, and the vertical axis represents sound pressure.

In particular, a sound wave is not detected when a water leakage hole does not exist, a relatively low peak sound pressure is detected at a 10 kHz frequency when the diameter of the water leakage hole 200 is 3.5 mm, and a relatively high peak sound pressure is detected at a 7.2 kHz frequency when the diameter of the water leakage hole 200 is 8.5 mm.

Figure 5:
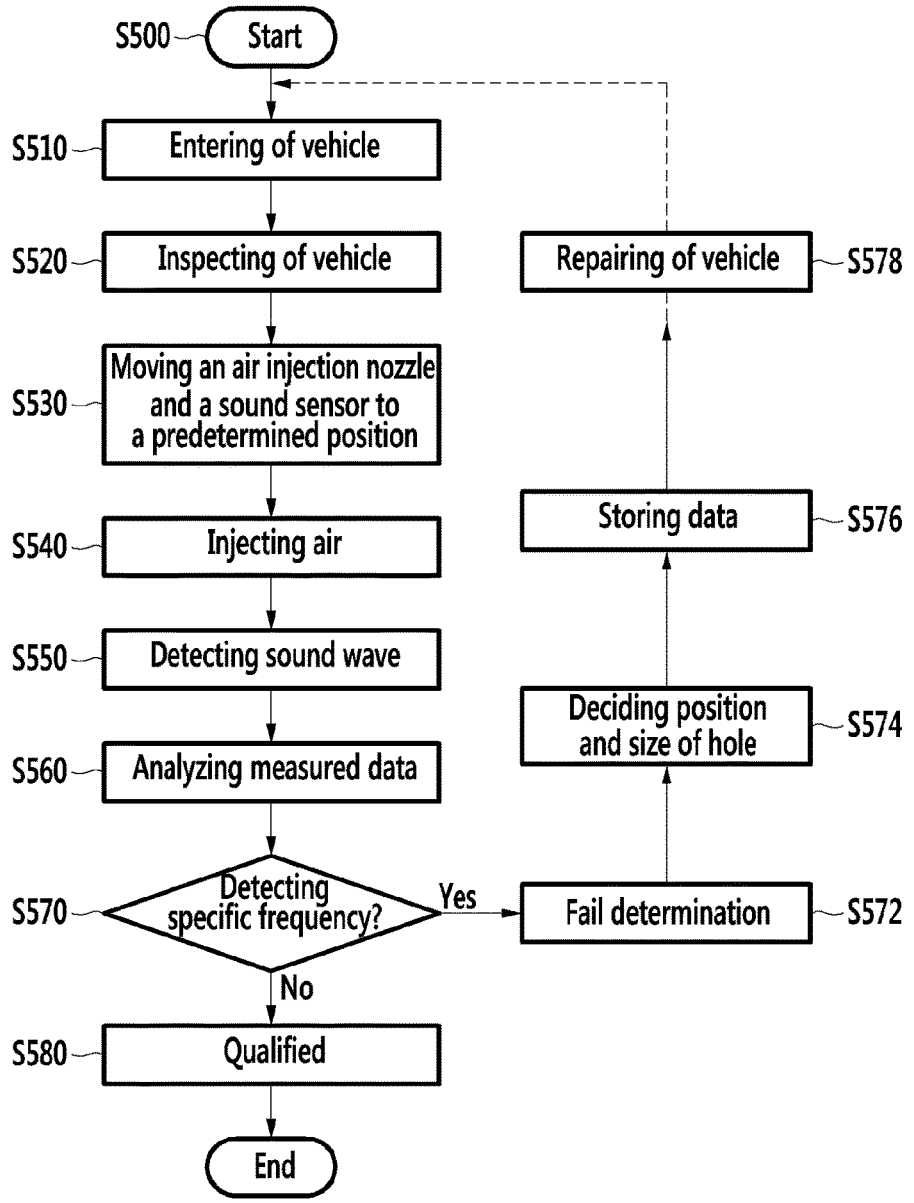
FIG. 5 is a flowchart showing a hole detection method of vehicle according to an exemplary embodiment of the present invention.

FIG. 5 is a flowchart showing a hole detection method of a vehicle according to an exemplary embodiment of the present invention.

Referring to FIG. 5, control is started at S500, and the vehicle enters a predetermined position at S510. A process for inspection of vehicle is started at S520.

The air injection nozzle 105 and the sound sensor 110 are moved to the predetermined position of the vehicle at S530. Here, the air injection nozzle 105 and the sound sensor 110 may be moved by the robot 117 or passively by a user.

Next, air is injected from the air injection nozzle 105 at S540. The air may be injected from the air injection nozzle 105 by an operator or automatically by the controller 100.

During injection of air, sound wave pressure is detected by the sound sensor at S550, and a detected and measured sound wave signal is analyzed at S560.

Next, whether a specific frequency is detected or not is decided at S570. Here, if a specific frequency is not detected, it is decided that a water leakage hole 200 is not formed on the vehicle body at S580, and the detecting process of water leakage parts is terminated at S590.

Meanwhile, if a specific frequency is detected, it is decided that a water leakage hole 200 is formed on the vehicle body 120 at S572, and a water leakage hole fail determination is made.

Further, a position and diameter of the water leakage hole 200 are calculated and selected at S574, the calculated and selected data is stored at S576, and the vehicle is repaired on the basis of the stored data at S578.

Figure 6:
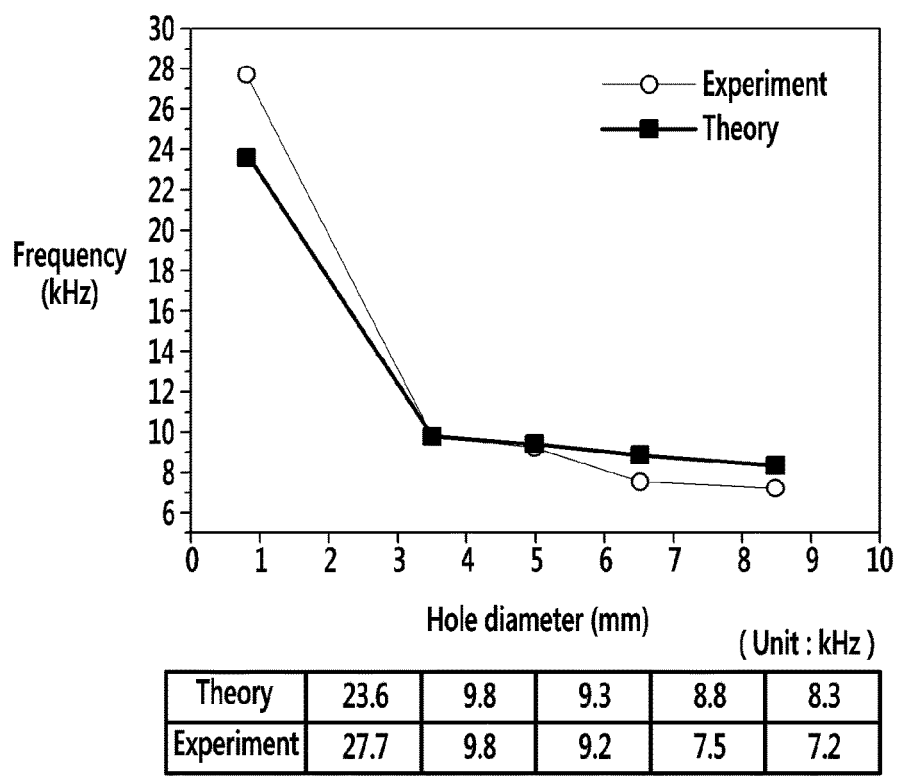
FIG. 6 is a graph showing a relationship of experimental values and theoretical values of a hole detection method of vehicle according to an exemplary embodiment of the present invention.

FIG. 6 is a graph showing a relationship of an experimental value and a theoretical value of a hole detection method of a vehicle according to an exemplary embodiment of the present invention.

Referring to FIG. 6, the horizontal axis represents a diameter of the water leakage hole, and the vertical axis represents a frequency of a detected sound wave.

As shown, the detected frequency is distributed according to the diameter of the water leakage hole 200, and the theoretical value and the experimental value have a similar pattern.

Figure 7:
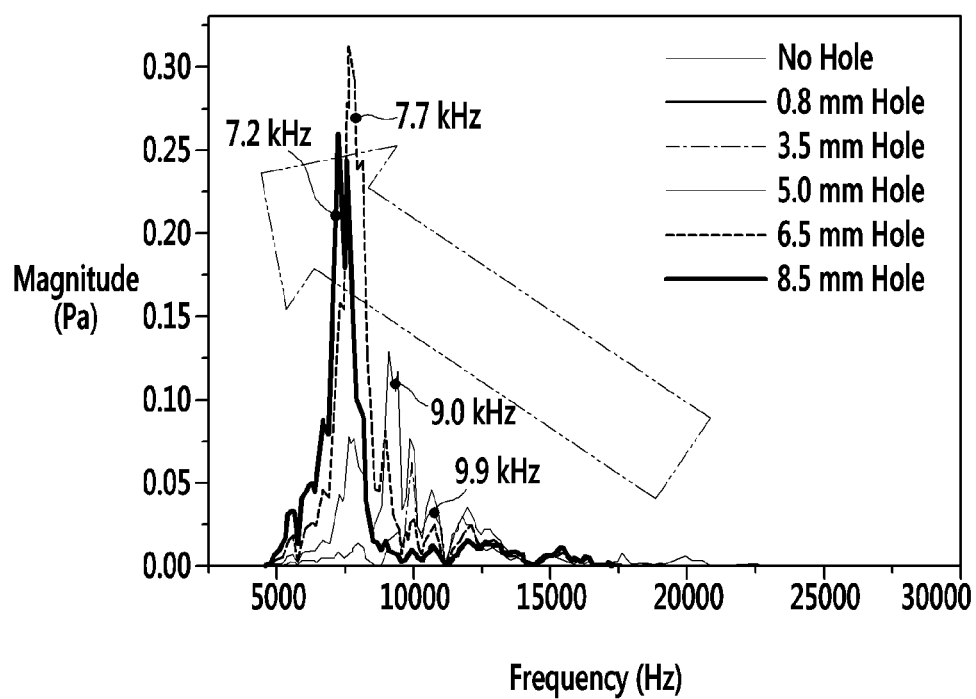
FIG. 7 is a graph showing a characteristic of a sound wave according to a size of a water leakage hole in a hole detection method of a vehicle according to an exemplary embodiment of the present invention.

FIG. 7 is a graph showing a characteristic of a sound wave according to a size of a water leakage a hole in hole detection method of a vehicle according to an exemplary embodiment of the present invention.

Referring to FIG. 7, the horizontal axis represents frequency, and the vertical axis represents sound pressure. Further, referring to the frequency and sound pressure according to the diameter of the water leakage hole 200, the diameter of the water leakage hole 200 may be selected and calculated.

Figure 8:
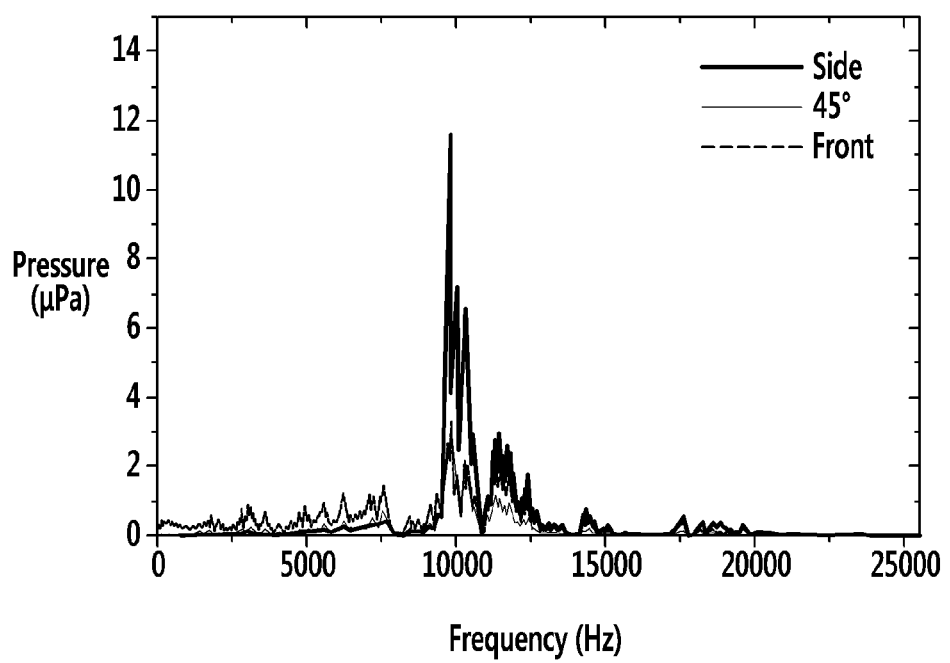
FIG. 8 is a graph showing a characteristic of a sound wave according to an injection angle of air injected from an air injection nozzle in a hole detection method of a vehicle according to an exemplary embodiment of the present invention.

FIG. 8 is a graph showing a characteristic of a sound wave according to an injection angle of air injected from an air injection nozzle in a hole detection method of vehicle according to an exemplary embodiment of the present invention.

Referring to FIG. 8, the horizontal axis represents frequency, and the vertical axis represents sound pressure. Further, the frequency and sound pressure according to the angle of air injected from the air injection nozzle 105 are shown.

"Side" denotes the state that the air injection nozzle 105 injects air in a perpendicular direction with respect to a thickness direction of the vehicle body 120, '45°' denotes the state that the air injection nozzle 105 injects air in a 45° inclined direction with respect to a thickness direction of the vehicle body 120, and 'Front' denotes the state that the air injection nozzle 105 injects air in a thickness direction of the vehicle body 120.

As shown, the frequency and sound pressure appear differently according to the air injection angle from the air injection nozzle 105, and it is preferable that the air injection nozzle 105 injects air in a perpendicular direction with respect to the thickness direction of the vehicle body 120.

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

What is claimed is:

1. A hole detection method of vehicle, comprising:
    positioning an air injection nozzle at a predetermined position of a vehicle body and positioning a sound sensor at a position corresponding to the air injection nozzle;
    injecting an air jet from the air injection nozzle and detecting a sound wave from the sound sensor; and
    calculating a characteristic of a water leakage hole formed on the vehicle body by using the sound wave detected from the sound sensor, wherein:
    the air injection nozzle is disposed at one surface of the vehicle body at a predetermined distance therefrom,
    the air injection nozzle injects air in a perpendicular direction with respect to a thickness direction of the vehicle body, and
    the sound sensor is disposed at an opposite side of the air injection nozzle on the basis of the vehicle body at a predetermined distance from the vehicle body.

2. The method of claim 1, wherein:
    the characteristic of the water leakage hole formed on the vehicle body is calculated by using output noise or frequency of the sound wave detected from the sound sensor.

3. The method of claim 1, wherein the characteristic of the water leakage hole is an interior diameter.

4. A hole detection system of a vehicle, comprising:
    an air injection nozzle disposed at a predetermined position of a vehicle body to inject an air jet;
    a sound sensor disposed to detect a sound wave generated by the air jet injected from the air injection nozzle; and
    a controller calculating existence or nonexistence and characteristics of a water leakage hole formed on the vehicle body according to characteristics of the sound wave detected from the sound sensor,
    wherein the air injection nozzle injects air in a perpendicular direction with respect to a thickness direction of the vehicle body.

5. The system of claim 4, wherein the system includes a moving portion set up to move the air injection nozzle or the sound sensor to a predetermined position of the vehicle body.

6. The system of claim 4, wherein the air injection nozzle and the sound sensor are disposed at opposite sides on the basis of the vehicle body and disposed at a predetermined distance therefrom.

7. The system of claim 4, wherein the characteristics of the water leakage hole formed on the vehicle body are calculated by using output noise or frequency of the sound wave detected from the sound sensor.

8. The system of claim 4, wherein the controller includes:
- an amplifier amplifying the sound wave detected from the sound sensor;
- a data processor processing data of the sound signal amplified by the amplifier; and
- a calculator calculating existence or nonexistence and the characteristics of the water leakage hole by using data processed at the data processor.

9. The system of claim 4, wherein the controller detects the characteristics of the sound wave detected from the sound sensor, and calculates existence or nonexistence and the characteristics of the water leakage hole formed on the vehicle body by comparing the detected sound wave characteristics and previously stored reference sound wave characteristics.

\* \* \* \* \*